United States Patent [19]

Higa et al.

[11] Patent Number: 4,895,853
[45] Date of Patent: Jan. 23, 1990

[54] ANTITUMOR ALKALOIDS

[75] Inventors: Tatsuo Higa, Naha, Japan; Ryuichi Sakai; Shigeo Kohmoto, both of Vero Beach; May S. Lui, Sebastian, all of Fla.

[73] Assignee: Harbor Branch Oceanographic Institution, Inc., Ft. Pierce, Fla.

[21] Appl. No.: 943,609

[22] Filed: Dec. 18, 1986

[51] Int. Cl.$^4$ ................. A61K 31/475; C07D 519/00; C07D 471/04
[52] U.S. Cl. .................................... 514/281; 514/292; 540/478; 540/481
[58] Field of Search ................. 540/478, 481; 546/87, 546/85, 86; 514/281, 286, 292

[56] References Cited

U.S. PATENT DOCUMENTS 4,575,508 3/1986 Steiner et al. ........................ 514/292
4,631,149 12/1986 Rinehart, Jr. et al. .............. 540/546

FOREIGN PATENT DOCUMENTS 0101574 2/1984 Fed. Rep. of Germany ........ 546/87

OTHER PUBLICATIONS

Rinehart, Jr., et al., J. Am. Chem. Soc., vol. 106, No. 5, pp. 1524-1526 (1984).
Kobayashi, et al., J. Am. Chem. Soc., vol. 106, No. 5, pp. 1526-1528, (1984).
Sakai, et al., J. Am. Chem. Soc., vol. 108, No. 20, pp. 6404-6405, (Oct. 1, 1986).
Johns, et al., Chemical Abstracts, vol. 69:77571u (1968).
Baslow, et al., Chemical Abstracts, vol. 73:64847w (1970).
Bossier, et al., Chemical Abstracts, vol. 75:72510n (1971).
Stempien, et al., Chemical Abstracts, vol. 86:95905m (1977).
Ballantine, et al., Chemical Abstracts, vol. 87:152455m (1977).
Targett, et al., Chemical Abstracts, vol. 102:76154v (1985).
Seldes, et al., Chemical Abstracts, vol. 103:120351g (1985).
Findlay, et al., Chemical Abstracts, vol. 103:211558w (1985).
Mebs, et al., Chemical Abstracts, vol. 104:63871w (1986).
Uemura, et al., J. Am Chem. Soc., vol. 107(16), pp. 4796-4798 (1985).
Nakamura, et al., Tetrahedron Letters, vol. 28, No. 6, pp. 621-624, 02/87.

Primary Examiner—Mukund J. Shah
Assistant Examiner—Diana G. Rivers
Attorney, Agent, or Firm—Carroll F. Palmer

[57] ABSTRACT

This invention relates to antitumor alkaloid compositions, a process of producing the compositions and a method for inhibiting tumors utilizing the compositions. More particularly, the compositions are antitumor alkaloids which are derived from marine organisms, i.e., the marine sponge Amphimedon sp.

10 Claims, No Drawings

ANTITUMOR ALKALOIDS

FIELD OF THE INVENTION

This invention relates to new cyclic organic compounds which have useful antitumor activity. More particularly, this invention relates to new cyclic alkaloid antitumor compositions derived from marine organisms, i.e., marine sponge, Amphimedon sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Marine organisms and particularly marine sponges are a potential source for chemically and biologically interesting molecules of great diversity. Some such molecules derived from sponges are described in Scheuer, P. J. Ed., *Marine Natural Products, Chemical and Biological Perspectives*; Academic Press; N.Y., 1978-1983; Vol. I-V; Faulkner, D. J. *Natural Products Reports* 1984, 551-598; Uemura, D.; Takahashi, K.; Yamamoto, T.; Katayama, C; Tanaka, J.; Okumura, Y.; Hirata, Y. *J. Am. Chem. Soc.* 1985, 107, 4796-4798. The entire disclosures of these references are hereby incorporated herein by reference.

Other interesting compositions derived from marine organisms (i.e., caribbean tunicate) and containing a βCarboline system are described in K. L. Rinehart, Jr., J. Kobayashi, G. C. Harbour, R. G. Hughes, Jr., S. A. Mizsak, T. A. Scahill, *J. Am. Chem. Soc.*, 106, 1524 (1984); J. Kobayashi, G. C. Harbour, J. Gilmore and K. L. Rinehart, Jr., ibid., at 1526.

Certain cyclic alkaloid compositions e.g. manzamine A derived from extracts of the marine sponge, Amphimedon sp. have been found to possess useful antitumor activity. A copending application of the present inventors, U.S. Ser. No. 879,094 filed June 26, 1986 is directed to antitumor alkaloid compositions, the entire disclosure of this copending application is hereby incorporated herein by reference. The present invention is also directed to useful antitumor alkaloid compositions which are derived from the marine sponge Amphimedon sp.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described herein, the invention comprises a composition of one of the general formulae (I-III):

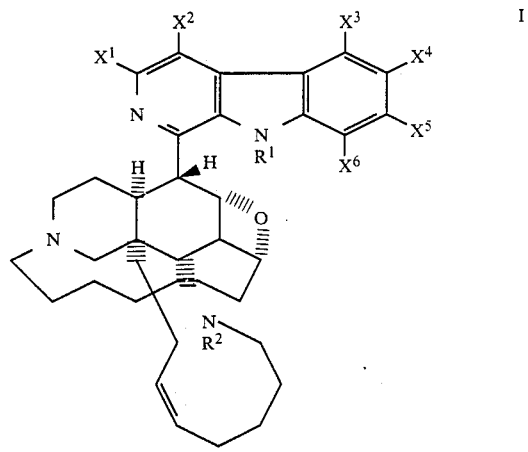

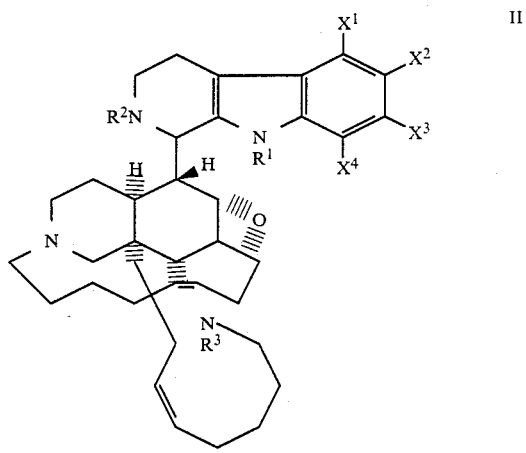

-continued

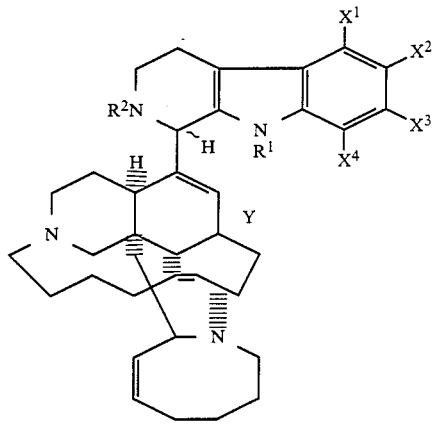

III wherein $X^1$, $X^2$, $X^3$, $X^4$, $X^5$, and $X^6$ are the same or different and are a hydrogen, halogen, hydroxyl, lower alkoxy, lower acyloxy, thiol, lower alkylthiol, nitro, amino, lower alkylsulfonyl, aminosulfonyl, hydroxysulfonyl(—SO₃H), lower acylamino, lower alkyl, or a lower monoalkyl or dialkyl amino group; $R^1$, $R^2$, and $R^3$ are the same or different and are a hydrogen, lower alkyl, or lower acyl group; and Y is a hydrogen, hydroxyl, lower alkyl, lower alkoxy, or lower acyloxy group.

Other embodiments of the invention include compositions according to formulae I–III wherein the double bonds are partially or fully reduced.

In further embodiments of the invention the composition is a mineral or organic acid salt of compositions according to formulae I–III or of compositions according to formula I–III wherein at least one double bond is reduced.

In preferred embodiments of the invention, the composition is substantially pure. In further preferred embodiments of the invention $R^1$, $R^2$, $X^1$, $X^2$, $X^3$, $X^4$, $X^5$, and $X^6$ are a hydrogen or hydroxy group.

In other embodiments of the invention, as fully described herein, the invention comprises a composition of one of the general formulae (IV and V):

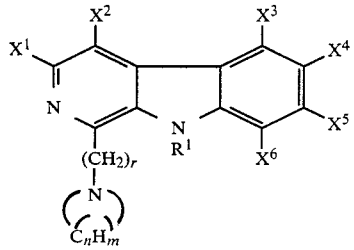

IV

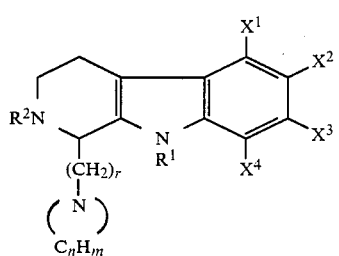

V wherein $X^1$–$X^6$, and $R^1$ and $R^2$ are the same as indicated above for formulae I–III and r is from 0 (zero) to 5; n is from 2 to 20; m is 2n, 2n −2, 2n −4 (n≧4), 2n −6 (n≧5), or 2n −8 (n≧8).

In more preferred embodiments of the invention, the invention comprises a composition of one of the following formulae, which are designated herein as manzamine B, C and D:

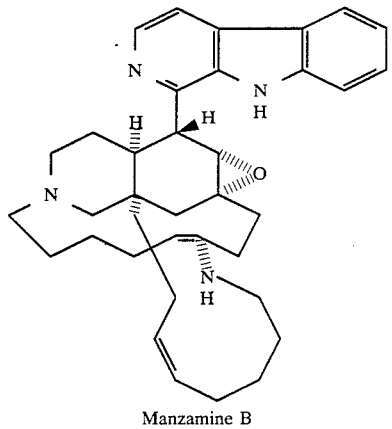

Manzamine B

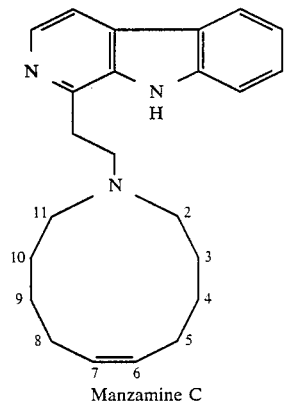

Manzamine C

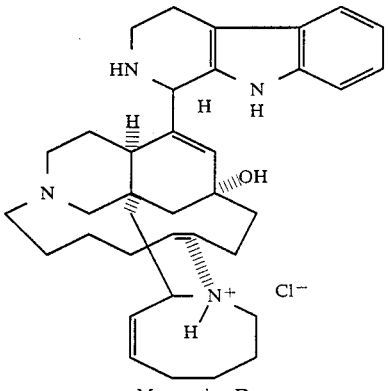

Manzamine D

As embodied and fully described herein, the invention also comprises an antitumor composition comprising, as active ingredient, an effective antitumor amount of one or more compositions according to formulae I–III; a composition according to formulae I–III wherein at least one double bond is reduced; an acid salt of a composition according to formulae I–III or an acid salt of a composition according to formulae I–III wherein at least one double bond is reduced: or a composition according to formulae IV or V; and a non-toxic pharmaceutically acceptable carrier or diluent.

In preferred embodiments the active ingredient comprises an effective amount of manzamine B, C or D.

As embodied and fully described herein, the invention also comprises a process to produce the compositions fo formulae I-III and their reduced or acid salt derivatives; formulae IV and V; and manzamine B, C and D. The process comprises the steps of collecting marine sponge Amphimedon sp.; contacting the sponge with at least one suitable organic solvent; concentrating the extract to an aqueous suspension; extracting the aqueous suspension with at least one suitable organic solvent to obtain an organic extract comprising a composition according to formulae I-III or their reduced or acid salt derivatives, or formulae IV or V; and isolating a composition according to formulae I-V or said acid salt or reduced derivatives of formulae I-III from the extract.

In preferred embodiments of the invention the suitable organic solvent is selected from the group consisting of acetone, methyl ethyl ketone, ethyl acetate, methanol, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I-III or their reduced or acid salt derivatives, or compositions of formulae IV or V.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formulae (I-III):

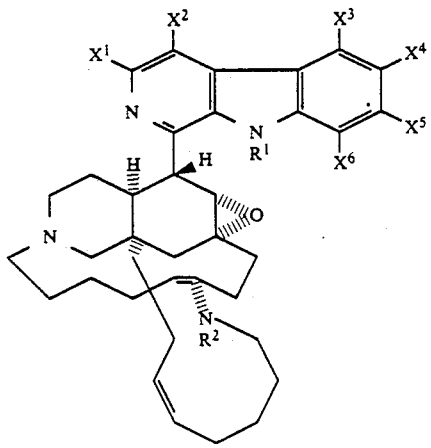

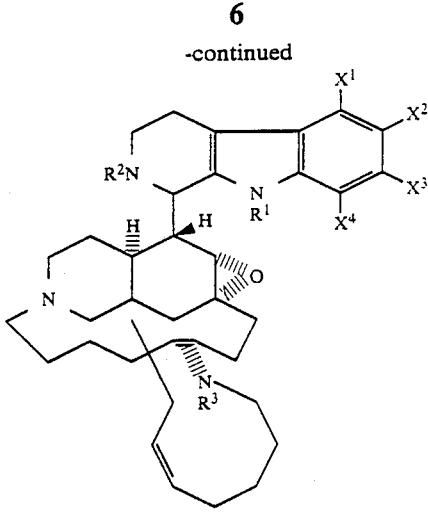

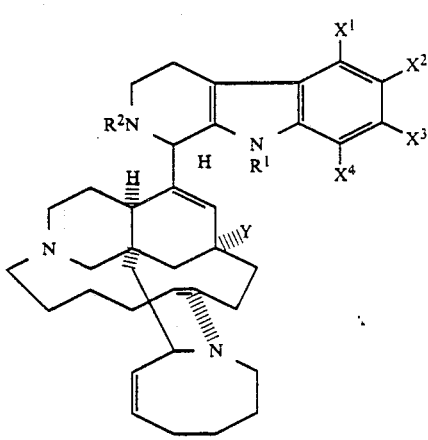

wherein $X^1$, $X^2$, $X^3$, $X^4$, $X^5$, and $X^6$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl ($-SO_3H$), lower acylamino, lower alkyl, or lower monoalkyl- or dialkyl-amino group; $R^1$ $R^2$ and $R^3$ are the same or different and are a hydrogen, lower alkyl, or lower acyl group; and Y is a hydrogen, hydroxyl, lower alkoxy, or lower acyloxy group.

In other embodiments of the invention the double bonds in the composition of formulae I-III are partially or fully reduced.

In further embodiments of the invention the composition is a mineral acid (e.g. HCl, $H_2SO_4$, $H_3PO_4$, $HNO_3$, etc.) or organic acid salt of compositions according to formulae I-III or of compositions according to formulae I-III wherein at least one double bond is reduced.

In other embodiments of the invention, as fully described herein, the invention comprises a composition of one of the general formulae (IV and V):

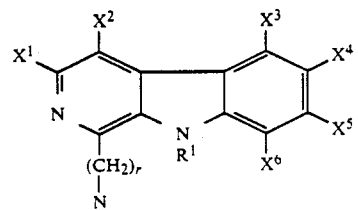

-continued

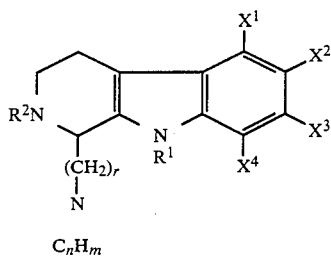

V

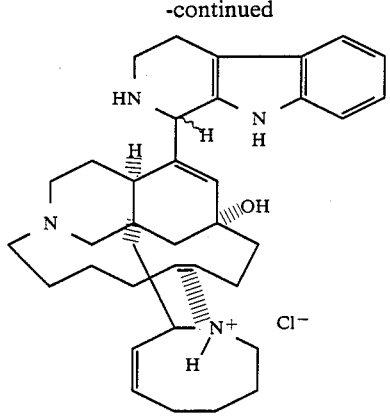

D wherein $X^1$–$X^6$ and $R^1$ and $R^2$ are the same as indicated above for formulae I–III and r is from 0 (zero) to 5; n is from 2 to 20; m is 2n, 2n −2, 2n −4 (n≧4), 2n −6 (n≧5), or 2n −8 (n≧8).

In more preferred embodiments of the invention, the invention comprises compositions designated as manzamine B, C or D of the formulae:

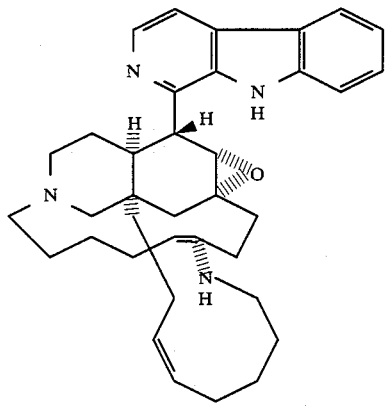

B

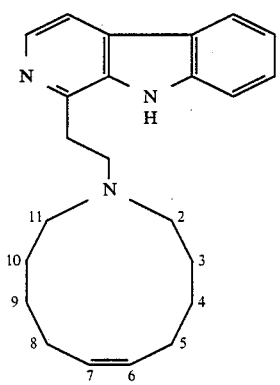

C

In accordance with the invention, an antitumor composition is provided comprising as active ingredient an effective antitumor amount of one or more of the compositions described above and identified by formulae I–III and their reduced or acid derivatives; formulae IV or V; or manzamine B, C or D; and a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. The compositions of the invention are active for inhibiting a diverse range of tumors and tumor cells including, but not limited to p-388 murine leukemia cells, human lung, colon and mammary tumors such as lung carcinoma A549, ileocecal adenocarcinoma HCT-8, human breast cancer cells MDAMB and other animal tumor and leukemia cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I or II and their reduced or acid derivatives, formulae IV or V; or manzamine B, C, or D. The effectiveness of the compositions of the invention for inhibiting tumors and tumor cells indicates their usefulness for controlling tumors in hosts including mammals and for treating cancerous cachexia.

In accordance with the invention, a process to produce compositions according to formulae I–III and their reduced or acid salt derivatives, formulae IV or V; or manzamine B–D is provided comprising the steps of: collecting marine sponge Amphimedon sp.; contacting the sponge with at least one suitable organic solvent to obtain an organic extract comprising a composition according to formulae I–III or their reduced or acid salt derivatives, formulae IV or V, or manzamine B, C or D; and isolating a composition according to formulae I–III or their reduced or acid salt derivative, formulae IV or V, or manzamine B, C or D.

A detailed description and explanation of a preferred embodiment of the process of the invention to produce the compositions according to formulae I–III and their reduced or acid salt derivatives, formulae IV or V or manzamine B, C or D is as follows:

The marine sponge Amphimedon sp. is collected by SCUBA off Manzamo, Okinawa. The sponge is cream colored both alive and preserved in ethanol, but appears white underwater. It is amorphous, approximately 20 cm in diameter and 5 cm in height. The surface of the sponge is smooth, with channelled depressions of various shapes leading to dermal and subdermal spaces. The sponge has sticky mucus which persists in the ethanol-preserved material. The consistency is soft and compressible, but difficult to cut or tear.

Identification of the sponge to the family Niphatidae and genus Amphimedon is based on microscopic examination of taxonomic voucher specimens deposited at the Indian River Coastal Zone Museum (Catalog No. 003:00025), Harbor Branch Oceanographic Institution, Inc, Ft. Pierce, Florida.

The ectosomal skeleton is a polygonally meshed, tangential reticulation of unispicular to multispicular fibers. The choanosomal skeleton is a radiating, multispicular reticulation with rectanglar and rounded meshes in which spongin dominates. Primary and secondary fibers can be distinguished, with diameters of 50–100 μm and 10–30 μm, respectively. The primary fibers barely protrude through the ectosome, resulting in an optically smooth surface. Spicules are smooth hastate oxea, slightly bent, with a size range of 100–170 μm in length by 5–10 μm in width. The marine sponge is contacted with and steeped in acetone as a first solvent for about 10 to 48 hours to obtain an extract which is concentrated to yield an aqueous suspension (the water is derived from the natural water content of the sponge). This step may be repeated to thoroughly extract the sponge and the additional aqueous suspensions may be combined. The aqueous suspension is then extracted with ethyl acetate as a second solvent to obtain an extract which comprises a composition according to formulae I–III or their reduced or acid salt derivatives, formulae IV or V, or manzamine B C or D. The ethyl acetate extract is concentrated to give a solid or gummy organic residue.

A portion of this residue was partitioned between the upper and lower layer of a solvent system e.g. heptane-dichloromethane-acetonitrile (50:15:35). Concentration of the upper and lower layer gives two oils. The oil from the lower layer was dissolved in methanol and the solution was kept in a refrigerator at about 5° C. overnight to induce crystallization of manzamine A. (see U.S. Ser. No. 879,094, supra) manzamine A was removed by filtration.

The mother liquor is subjected to separation such as by counter current chromatography (CCC) using ethyl acetate-heptane-methanol-water to give three mobile phase fractions and one stationary phase which comprise compositions according to formulae I–III or their reduced or acid salt derivatives, formulae IV or V, and manzamine B, C or D.

While acetone and ethyl acetate are the presently preferred choices for the first and second extracting solvents, respectively, other suitable solvents may be substituted. A suitable solvent should be capable of extracting a compound according to any one of formulae I or II or their reduced or acid salt derivative, formulae IV or V or manzamine B, C or D from other components of the marine sponge. Suitable first and second solvents which may be substituted for either acetone or ethyl acetate include, but are not limited to, the following organic solvents: methyl ethyl ketone; acetone; methanol; ethanol; methyl isobutyl ketone; methylene chloride; chloroform; ether; and tetrahydrofuran.

Any suitable fractionation and isolation techniques may be utilized to isolate and purify the compositions of the invention prepared in accordance with the processes of the invention. Suitable fractionation techniques include various chromotography techniques such as, high pressure liquid chromatography (HPLC) with a suitable column as would be known to those skilled in the art including silica gel, Sephadex LH-20; ammonia-treated silica gel; RP-18, RP-8, and Li-Chrosorb $NH_2$ column. These columns are eluted with suitable eluents such as: heptane; ethyl acetate; methylene chloride; methanol; isopropyl alcohol; and various combinations and ratios thereof as would be known to those skilled in the art. Countercurrent chromatography techniques are also useful for isolating compositions of the invention an example of which is included, infra.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

Examples 1–5

The antitumor cyclic alkaloids of the invention were prepared from a marine sponge, Amphimedon sp., according to the following procedures.

Examples 1–3

Preparation of Manzamine B–D

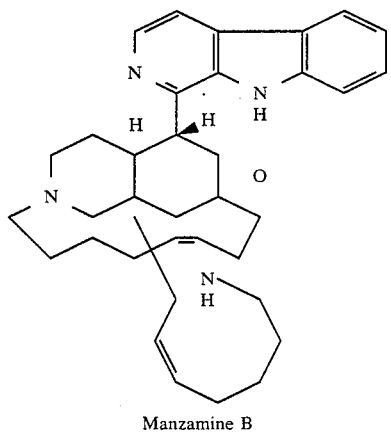

Manzamine B

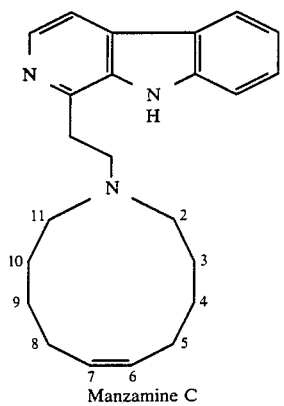

Manzamine C

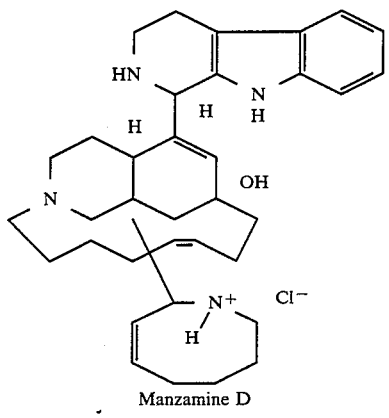

Manzamine D

A sample (8 kg) of the sponge Amphimedon sp. was collected by SCUBA off Manzamo, Okinawa. The sample was soaked in acetone (6 liters) overnight, and the extract was decanted. The sponge was extracted two more times in the same manner. The combined extracts were concentrated to aqueous suspension which was extracted with ethyl acetate (500 ml×4). The ethyl acetate extract was dried over anhydrous sodium sulfate and concentrated to furnish 30 gms of gummy residue. A portion (26 gms) of this residue was partitioned between the upper and lower layer of the solvent system composed of heptane-dichloromethane-acetonitrile (50:15:35). Concentration of the upper and lower layer gave 10.9 and 15.0 gms of oils, respectively. The oil from the lower layer was dissolved in methanol (20 ml), and the solution was kept in a refrigerator at 5° C. overnight to induce crystallization of manzamine A. Crude crystals (5 gms) of manzamine A was obtained by filtration.

The mother liquor was subjected to separation with counter current chromatography (CCC) using ethyl acetate-heptane-methanol-water (7:4:4:3, mobile phase: upper layer) to give three mobile phase fractions and one stationary phase (1.56 gms). Fraction 1 (3.27 gms) contained manzamine A and lipids, fraction 2 (1.65 gms) manzamine B and lipids, and fraction 3 (1.56 gms) manzamine C and lipids. Fraction 2 was further separated by CCC under the same conditions into 26 mobile-phase fractions and one stationary-phase fraction. Fractions (13-16) and the stationary phase which contained manzamine B was then subjected to chromatography on polystyrene gel (methanol) and on silica gel (chloroform-acetonitrile-2- propanol 400:40:1) to give a crude sample (154 mg) of manzamine B as an oil. The oil was purified by HPLC using a Hibar-NH2 column (ethyl acetate) to furnish 110 mg of colorless solid. Recrystallization from ethyl acetate afforded 76 mg of manzamine B as colorless crystals.

The stationary phase (1.56 gms) from the first CCC separation was chromatographed on silica gel with chloroform-acetonitrile-2-propanol (20:5:2) giving three fractions (1, 2 and 3). Repeated recrystallization of fraction 2 (248 mg) from chloroform-acetonitrile gave 86 mg of manzamine C as colorless plates. Fraction 1 which contained manzamine B and D was further separated on polystyrene gel (MeOH) and then by HPLC (Hibar Si-60, chloroform-methanol 4:1) to furnish manzamine B (50 mg) and a crude sample of manzamine D. The latter was purified by running on HPLC (Hibar Si-60, chloroform-methanol-2-propanol 5:1:1) to afford 115 mg of manzamine D as a pure solid.

Manzamine B

Mp 198°-203° C., $[\alpha]_D^{20}+89°$ (c 1.8, CHCl$_3$). IR (film) 3340, 3200, 3140, 3060, 3000, 2920, 2845, 1620, 1510, 1495, 1470, 1445, 1420, 1400, 1325, 1275, 1255, 1235, 1210, 1120, 870, 745, 710, 660 and 620 cm$^{-1}$. UV (MeOH) $\lambda_{max}$ 212, 235, 240 sh, 250 sh, 282 sh, 288, 338, and 350 nm. $^1$H NMR (CDCl$_3$) δ11.45 (1 H, s), 8.26 (1 H, d, J=5 Hz), 8.07 (1 H, d, J=7.8 Hz), 7.84 (1 H, d, J=5 Hz), 7.46 (1 H, dd, J=7.8, 7.8 Hz), 7.40 (1 H, d, J=7.8 Hz), 7.18 (1 H, dd, J=7.8, 7.8 Hz), 5.62 (1 H, ddd, J=10.8, 10.8, 5.4 Hz), 5.47 (1 H, ddd, J=10.8, 10.8, 4.3 Hz), 5.30 (2 H, br s), 3.80 (1 H, dd, J=9.5, 4.5 Hz), 3.52 (1 H, d, J=4.4 Hz), 3.47 (1 H, m), 3.09 (1 H, br), 2.95 (1 H, s), 2.80 (2 H, m), 2.6−1.4 (complex), 1.30 (1 H, dd, 13.2, 13.2 Hz), 1.14 (1 H, d, J=13.9 Hz), and 0.92 (1 H, dd, J=13.9, 7.9 Hz). $^{13}$C NMR (CDCl$_3$) δ 146.24 (s), 140.48 (s), 137.02 (d), 134.87 (s), 132.34 (d), 131.83 (d), 131.32 (d), 129.22 (s), 128.83 (d), 127.66 (d) 121.33 (d), 121.10 (s), 118.79 (d), 113.71 (d), 111.33 (d), 60.39 (s), 60.23 (d), 59.71 (d), 56.55 (t), 50.81 (t) 47.50 (t), 44.53 (d) 43.99 (s), 39.44 (t), 32.48 (d) 32.25 (t), 27.87 (t), 27.77 (t), 26.66 (t), 24.32 (t), 23.54 (t), 23.41 (t), 22.68 (t), 18.61 (t) and 18.09 (t).

Manzamine C

Mp 77°-82° C., $[\alpha]_D^{20}$ 0 (c 0.6, CHCl$_3$). UV (MeOH) $\lambda_{max}$ 212 ($\epsilon$13500), 234 (22000), 239 sh (21,000), 248 sh (14,000), 282 sh (6100), 287 (9500), 335 (3000) and 348 nm (3000). IR (KBr) 3000, 2910, 2840, 2810, 1640, 1495, 1465, 1440, 1425, 1350, 1325, 1320, 1290, 1230, 1215, 1200, 1120, 740, and 715 cm$^{-1}$. $^1$H NMR (CDCl$_3$) δ12.76 (1 H, s, D$_2$O exchangeable), 8.26 (1 H, d, J=5 Hz), 8.11 (1 H, d, J=7.8 Hz), 7.81 (1 H, d, J=5 Hz), 7.51 (2 H, m), 7.34 (1 H, m), 5.47 (2 H, m), 3.31 (2 H, dd, 5.1, 5.1 Hz), 2.90 (2 H, dd, J=5.1, 5.1 Hz), 2.82 (4 H, dd, J=7.5, 7.5 Hz), 2.32 (4 H, m), 1.75 (4 H, m), and 1.52 (4 H, m). $^{13}$C NMR (CDCl$_3$) δ145.78 (s), 140.57 (s), 137.36 (d), 135.51 (s), 130.90 (d, 2 C), 128.13 (s), 127.56 (d), 121.90 (s), 121.64 (d), 119.02 (d), 112.98 (d), 111.76 (d), 52.76 (t), 48.90 (t, 2 C), 34.68 (t), 25.99 (t, 2 C), 24.91 (t, 2 C), and 23.26 (t, 2 C).

Manzamine D

Mp 165°-168° C., $[\alpha]_D^{20}+60.6°$ (c 0.66, CHCl$_3$). HR EIMS m/z 552.3837 (calcd for C$_{36}$H$_{48}$N$_4$O 552.3828). LR EIMS m/z 552 (94), 534 (23), 522 (25), 504 (30), 494 (6), 442 (6), 430 (8), 429 (10), 427 (8), 411 (8), 399 (18), 381 (22), 379 (45), 351 (8), 256 (9), 197 (9), 171 (68), 162 (100), 144 (28), 130 (13), and 110 (16 rel %). UV (MeOH) $\lambda_{max}$ 223 ($\epsilon$28800), 275 sh (6300), 281 (6700), and 288 nm (5400). IR (CCl$_4$) 3460, 3000, 2920, 1450, 1440, 1365, 1340, 1290, 1240, 1210, 1145, 1105, 1070, 995, and 970 cm$^{-1}$. $^1$H NMR (C$_6$D$_6$+CD$_3$OD) δ7.49 (1 H, d, J=7.6 Hz), 7.42 (1 H, J=7.9 Hz), 7.14 (1 H, t, J=7.5 Hz), 7.08 (1 H, t, J=7.3 Hz), 5.85 (1 H, m), 5.71 (1 H, s), 5.64 (1 H, m), 5.52 (1 H, m), 5.20 (1 H, dd, J=9.3, 9.8 Hz), 4.51 (1 H, s), 4.18 (1 H, t, J=7.8 Hz), 3.40 (1 H, s), 3.16 (1 H, m), 2.98 (2 H, m), 2.81 (2 H, m), 2.62 (2 H, m), 2.51 (1 H, m), 2.35 (2 H, m), and 2.2−1.2 (complex). $^{13}$C NMR (CDCl$_3$) δ 141.03 (s), 136.36 (d), 135.39 (s), 134.49 (d), 133.77 (s), 132.17 (d), 129.82 (d), 128.66 (d), 127.70 (s), 121.38 (d), 119.21 (d), 117.98 (d), 110.95 (d), 109.35 (s), 75.50 (d), 69.80 (s), 68.77 (t), 60.03 (d), 55.09 (d), 53.59 (t), 51.01 (t), 49.83 (t), 47.59 (s), 44.78 (t), 43.58 (t), 40.94 (t), 37.93 (d), 33.27 (t), 32.04 (t), 28.44 (t), 27.08 (t), 26.16 (t), 25.94 (t), 22.65 (t), and 21.92 (t).

Example 4—Preparation of Reduced Derivative

Manzamine B and D are easily reduced to dihydro-, tetrahydro- or hexahydromanzamine B and D, respectively, by employing one, two, or three molar equivalents of hydrogen, respectively, in catalytic reduction. A sample of manzamine B or D and a small amount of catalyst such as Pd/C, Pt/C, or Raney Ni are mixed in a suitable solvent such as ethanol or methanol. The mixture is stirred in the presence of hydrogen in a hydrogenation apparatus. If the reaction is too slow, it can be facilitated by making the media slightly acidic by addition of a trace amount of acid such as HCl. When full reduction to prepare hexahydromanzamine B or D is desired, the reduction is carried out under elevated pressure of hydrogen using an apparatus such as a Parr hydrogenation apparatus.

Example 5—Preparation of Acid Salt

Since manzamine B is a basic compounds, its acid salt is easily prepared by mixing manzamine B with an inorganic acid such as HCl, H$_2$SO$_4$, or an organic acid such as oxalic acid in aqueous ethanol or methanol.

ANTITUMOR ACTIVITIES OF THE COMPOUNDS OF THE INVENTION

The following assay method was utilized to illustrate the antitumor effectiveness of the compositions of Formulae I-V corresponding to manzamines B-D of the examples.

P388 MOUSE LEUKEMIA CELL ASSAY

Maintenance of Cell Line

P388 mouse leukemia cells are grown in Dulbecco MEM medium with 10% horse serum, 4 mM glutamine, and 20 ug/ml gentamycin (Biologos, Inc.). Cells are incubated in 10% CO$_2$ and subcultured 2 times per week.

PROCEDURE

1. Add compound to each well of a 24-well plate or tube and allow solvent to evaporate to dryness.
2. Add 2 ml (1.2×10$^5$) cells to each well or tube and mix.
3. Incubate in 10% CO$_2$ at 37° for 48 hours.
4. Read platees with an inverted microscope, scoring activity from 1+ to 4+ as follows: ND (not detectable), >90%; 1+, 75-90%; 2+, 50-74%; 3+, 25-49%; 4+, <25% of control growth. Cell counts are performed on each tube and results are reported as percent of control. Alternatively, scoring may be expressed as IC$_{50}$ which represents the minimum concentration of the composition required to inhibit 50% of the cell growth on the plate. Cell counts are performed on each tube and results are reported as percent of control.

The results of the above assay are summarized in Table 1.

TABLE 1

| Antitumor Assay Results of Manzamine B-D | |
|---|---|
| Composition | P388 IC$_{50}$ (μg/ml) |
| Manzamine   A | 0.075 |
| B | 6.0 |
| C | 3.0 |
| D | 0.5 |

Table 1 shows that manzamines B-D have good antitumor activity at concentrations of at least 6 ug/ml against mouse leukemia cells.

It is apparent from the in vitro testing that the compositions of the invention, are effective for inhibiting or destroying tumor cells and tumors and therefore controlling diseases caused by or related to such tumors in hosts such as cancerous cachexia in fulfillment of the objects of the invention.

The scope of the present invention is not limited by the description, examples, and suggested uses herein and modifications can be made without departing from the spirit of the invention. For example, it may be noted that other derivatives of the compositions of examples 1-3 such as halogenated derivatives may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A substantially pure compound according to any one of the following formulae I, II, III or IV:

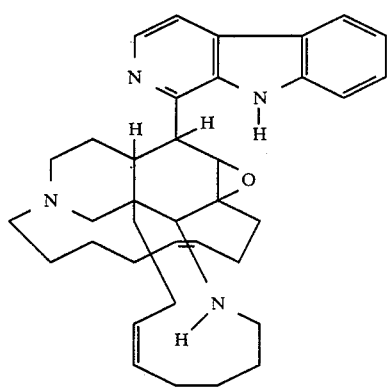

I

-continued

II

[Structural formula II - indole-containing polycyclic compound with epoxide]

III

[Structural formula III - indole-containing polycyclic compound with OH group]

IV

[Structural formula IV showing indole linked via —CH₂—CH₂—N— to —C₁₀H₁₈]

and acid salts thereof.

2. A substantially pure compound according to the formula:

[Structural formula of compound]

the dihydro and tetrahydro derivatives thereof and acid salts thereof.

3. A substantially pure compound of the formula:

[Structural formula of compound]

4. A substantially pure compound of the formula:

[Structural formula of compound]

5. A substantially pure compound of the formula:

[Structural formula of compound]

6. A pharmaceutical composition comprising, as an active ingredient, in an amount effective to provide a dosage of between about 0.01 and 100 micrograms of one or more of compounds of claim 1 and a non-toxic pharmaceutically acceptable carrier or diluent.

7. A pharmaceutical composition comprising, as an active ingredient, in an amount effective to provide a dosage of between about 0.01 and 100 micrograms of one or more of compounds of claim 2 and a non-toxic pharmaceutically acceptable carrier or diluent.

8. A pharmaceutical composition comprising, as an active ingredient, in an amount effective to provide a dosage of between about 0.01 and 100 micrograms of one or more of the compounds of claim 3 and a non-toxic pharmaceutically acceptable carrier or diluent.

9. A pharmaceutical composition comprising, as an active ingredient, in an amount effective to provide a dosage of between about 0.01 and 100 micrograms of one or more of the compounds of claim 4 and a non-toxic pharmaceutically acceptable carrier or diluent.

10. A pharmaceutical composition comprising, as an active ingredient, in an amount effective to provide a dosage of between about 0.01 and 100 micrograms of one or more of the compounds of claim 5 and a non-toxic pharmaceutically acceptable carrier or diluent.

* * * * *

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 2:  structure I:  should read

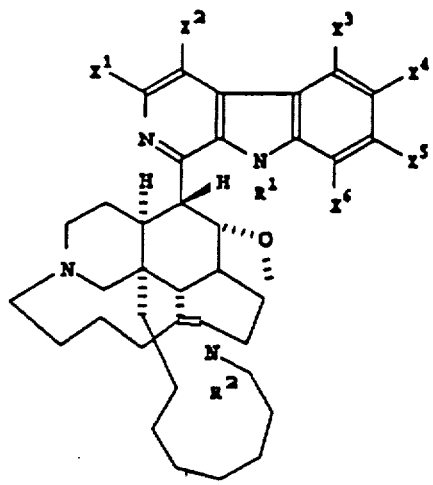 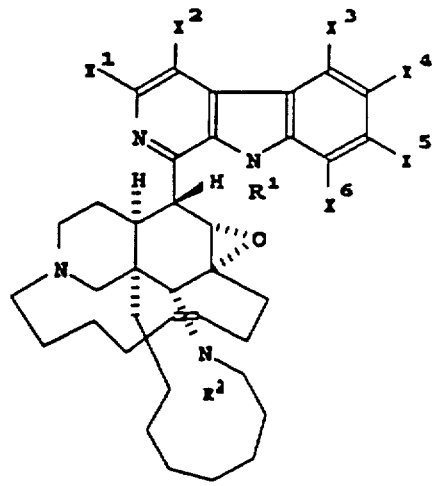

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 2:    structure II:    should read

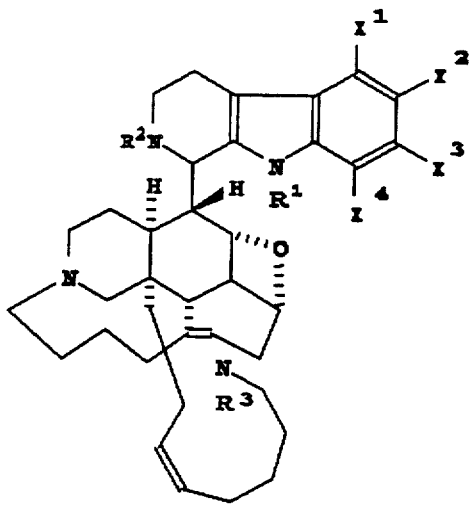 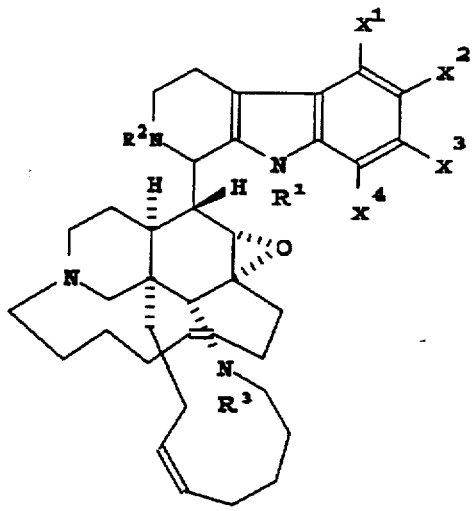

UNITED STATES PATENT AND TRADEMARK OFFICE
CERTIFICATE OF CORRECTION

Page 3 of 19 pages

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 3: structure III: should read

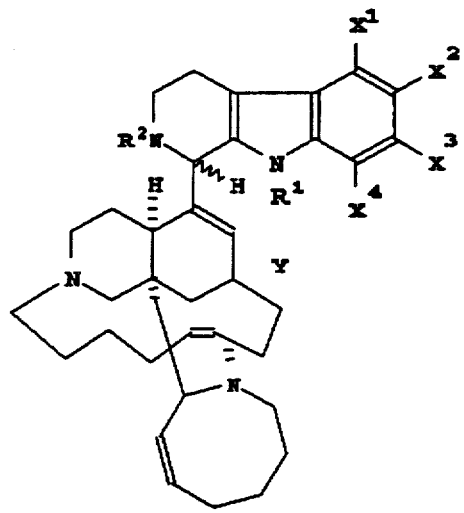 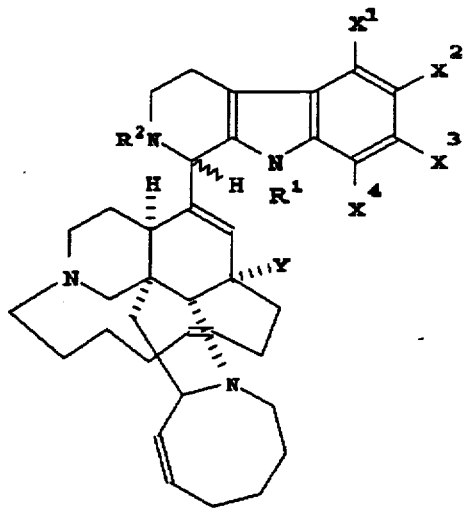

UNITED STATES PATENT AND TRADEMARK OFFICE
CERTIFICATE OF CORRECTION

Page 4 of 19 pages

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 3:   structure IV:                    should read

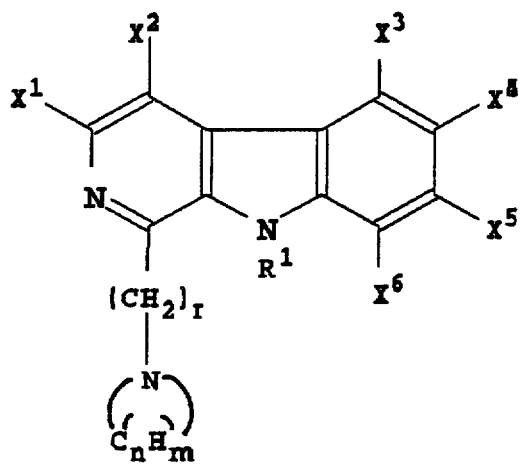   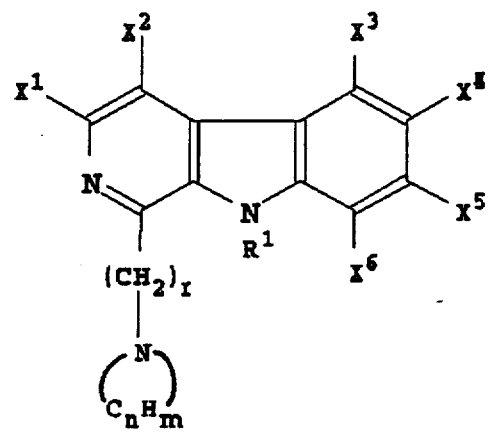

UNITED STATES PATENT AND TRADEMARK OFFICE
CERTIFICATE OF CORRECTION

Page 5 of 19 pages

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 4:          Manzamine B:                should read

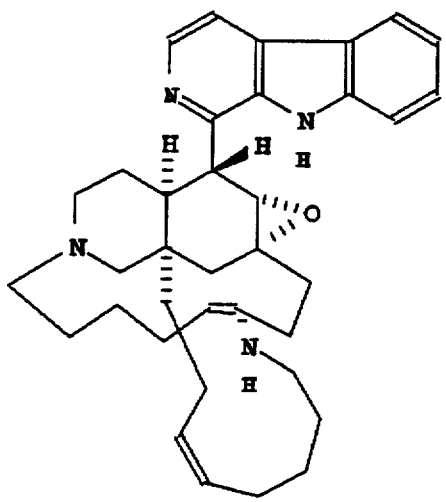 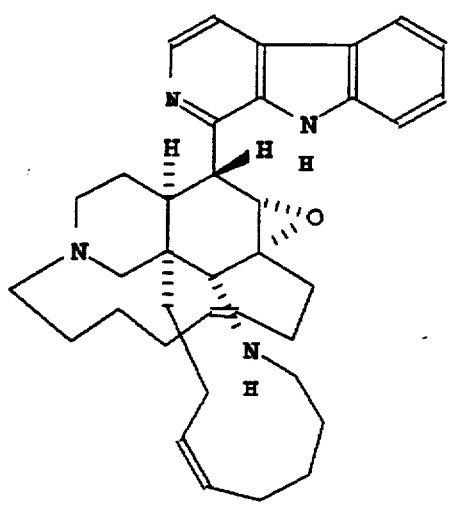

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 4:     Manzamine D:                    should read

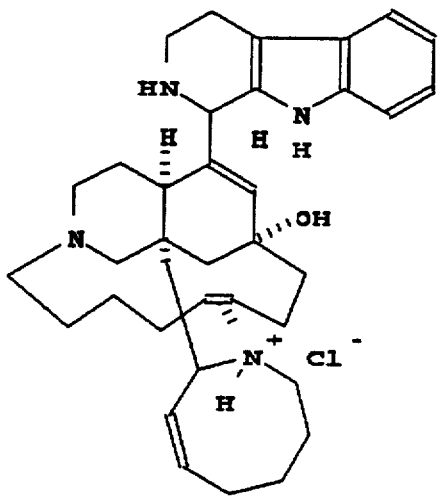 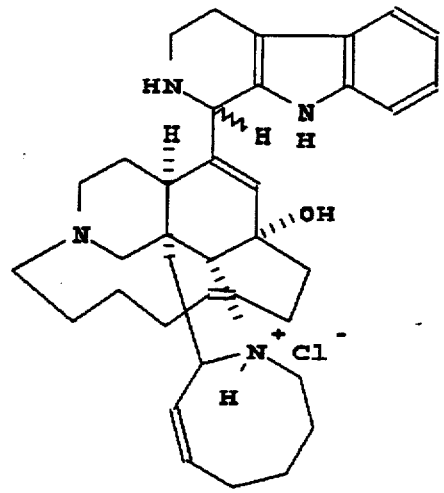

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 5:   structure I:   should read

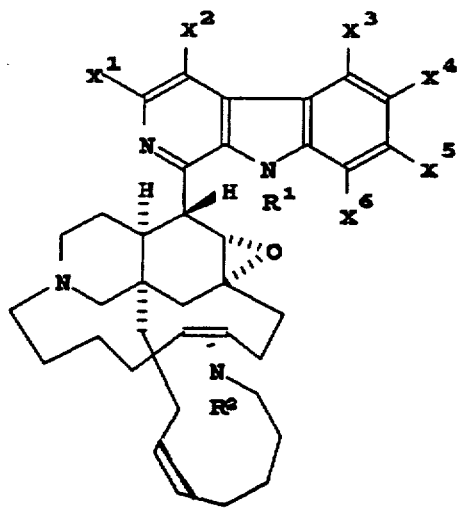 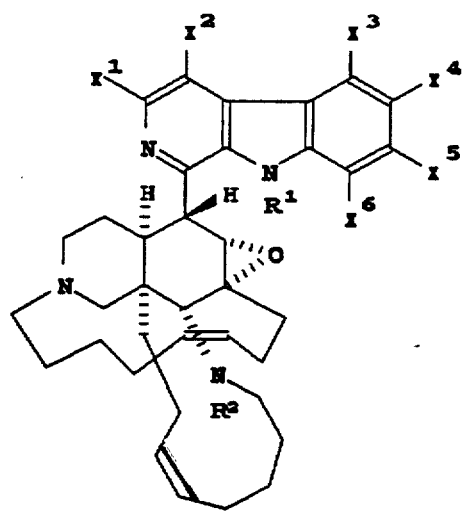

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 6:     structure II:     should read

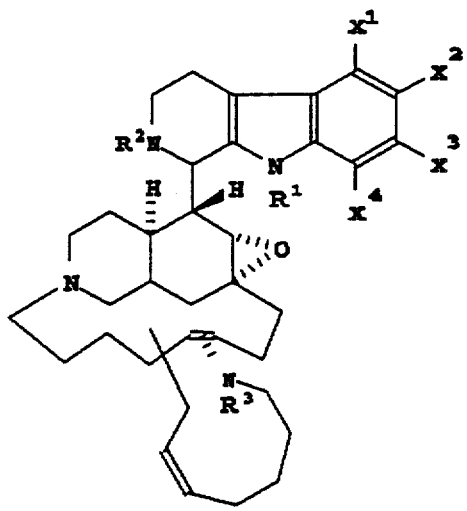 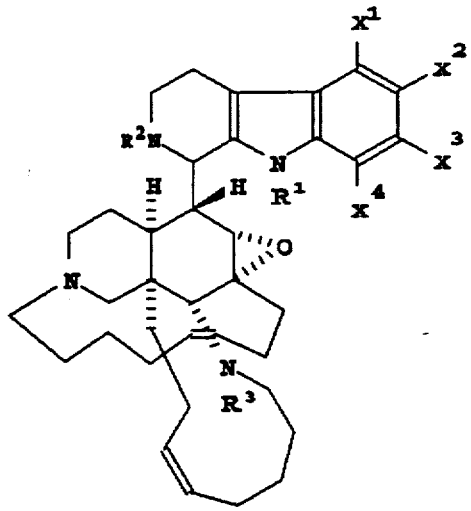

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 6:       structure III:          should read

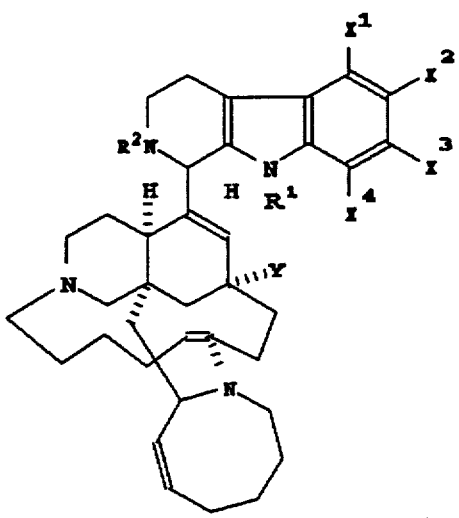 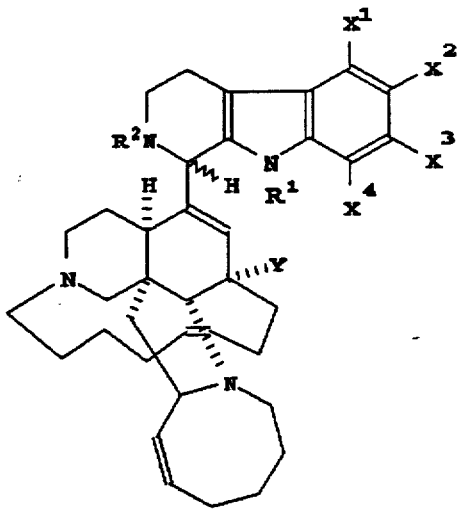

UNITED STATES PATENT AND TRADEMARK OFFICE
CERTIFICATE OF CORRECTION

PATENT NO.   :   4,895,853

DATED        :   January 23, 1990

INVENTOR(S)  :   Tatsuo Higa, Ryuichi Sakai, Shigeo Kohmoto, May S. Lui

It is certified that error appears in the above-identified patent and that said Letters Patent is hereby corrected as shown below:

Column 6:       structure IV:       should read

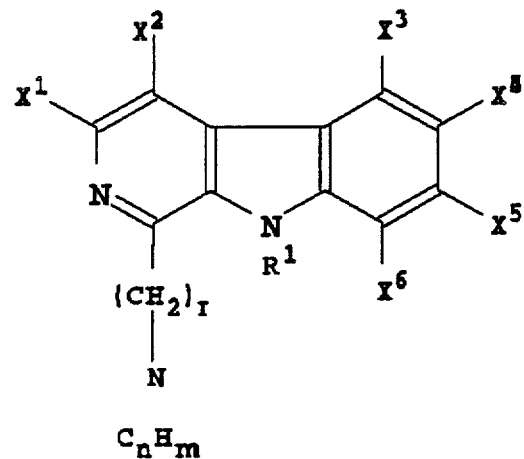     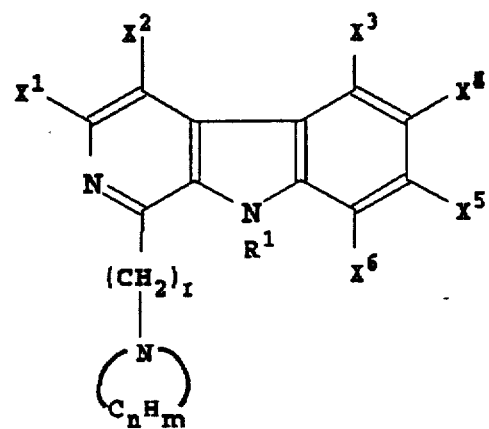

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 7:   structure V:   should read

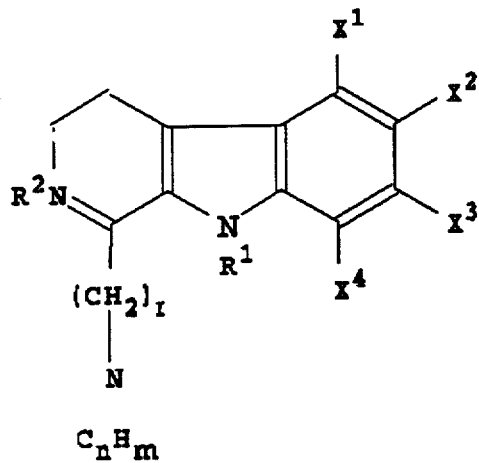 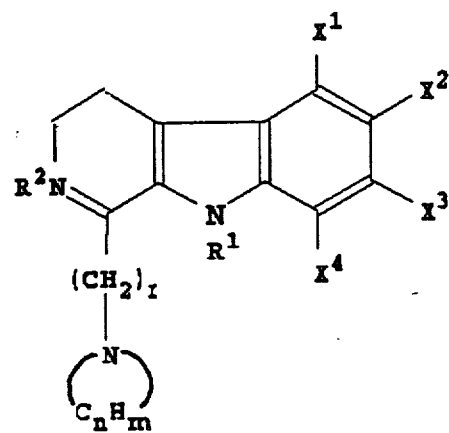

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 7:  structure B:  should read

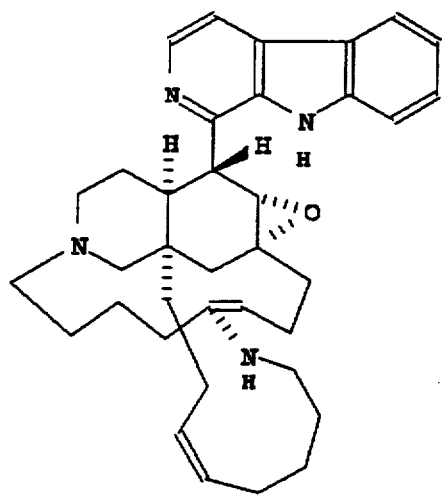 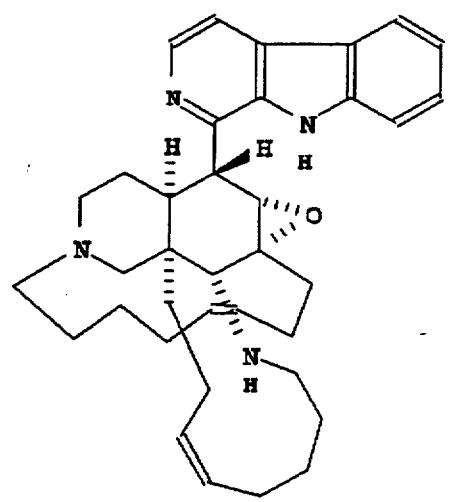

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 8:  structure D:  should read

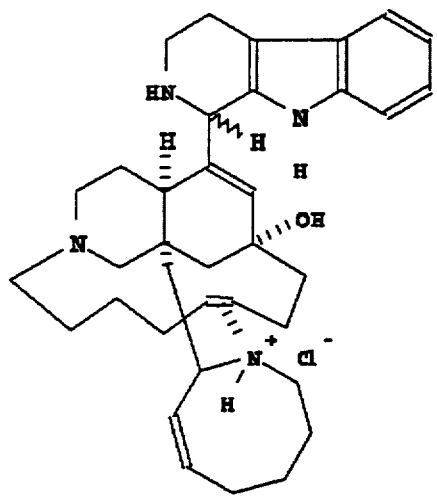   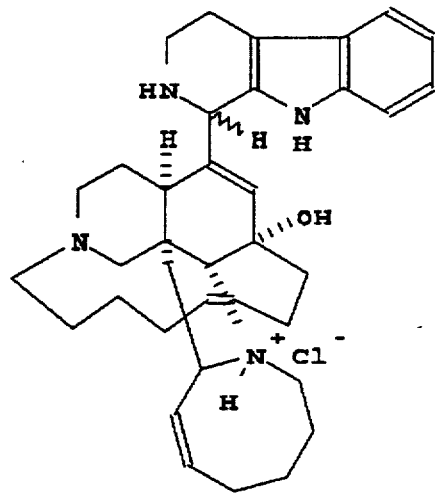

UNITED STATES PATENT AND TRADEMARK OFFICE
CERTIFICATE OF CORRECTION

Page 14 of 19 pages

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 10: Manzamine B:                    should read

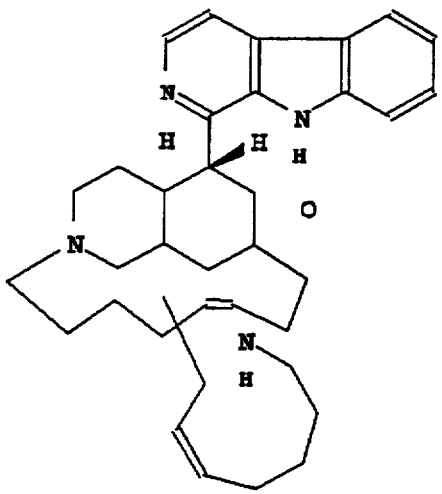 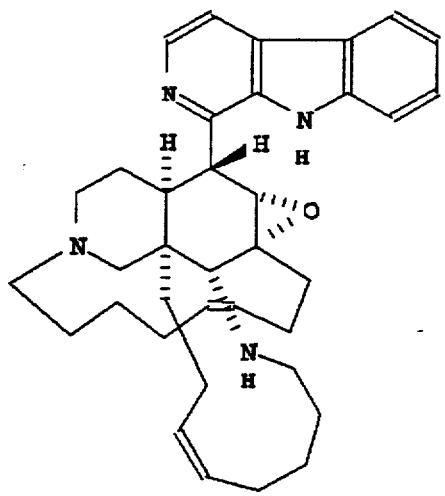

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 11: Manzamine D:               should read

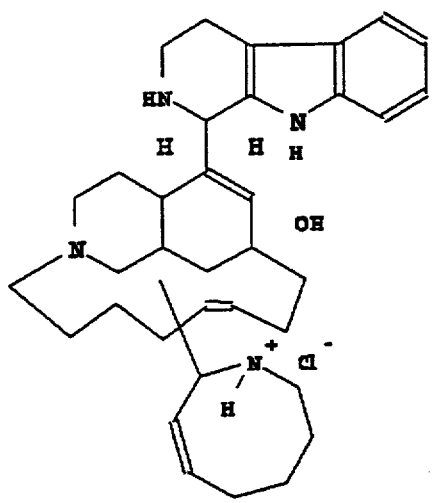 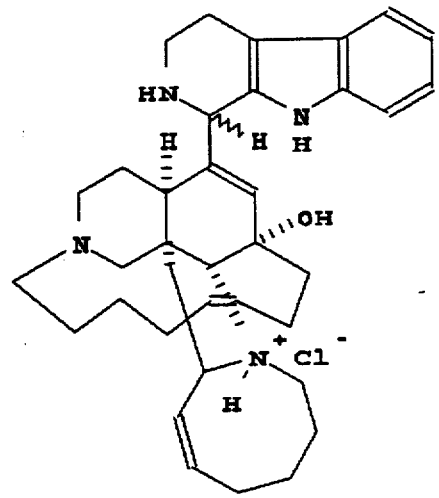

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 15: claim 1, structure IV:     should read

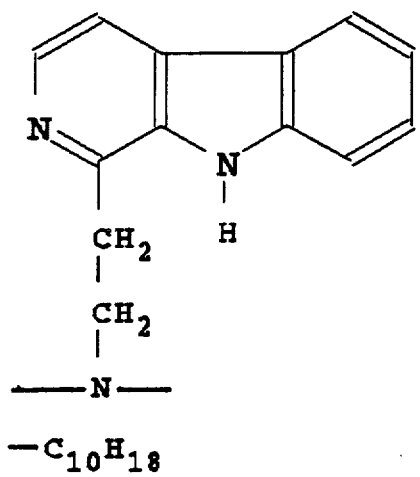     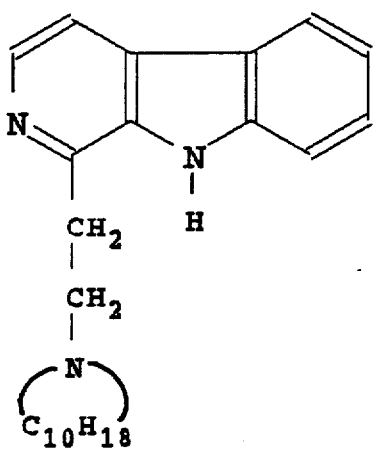

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 15: Claim 2:                    should read

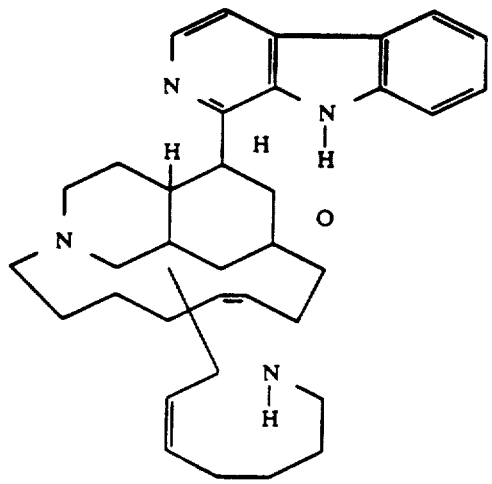 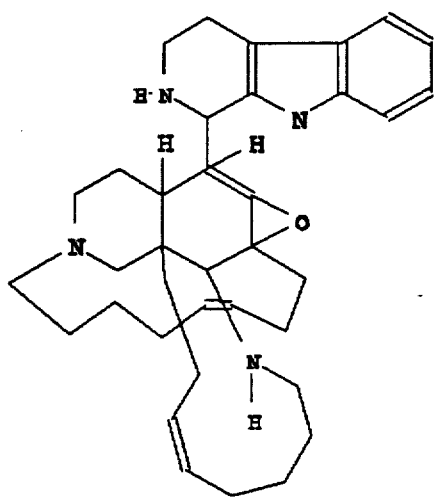

UNITED STATES PATENT AND TRADEMARK OFFICE
CERTIFICATE OF CORRECTION

PATENT NO. : 4,895,853

DATED : January 23, 1990

INVENTOR(S) : Tatsuo Higa, Ryuichi Sakai, Shigeo Kohmoto, May S. Lui

It is certified that error appears in the above-identified patent and that said Letters Patent is hereby corrected as shown below:

Column 16: Claim 3:                   should read

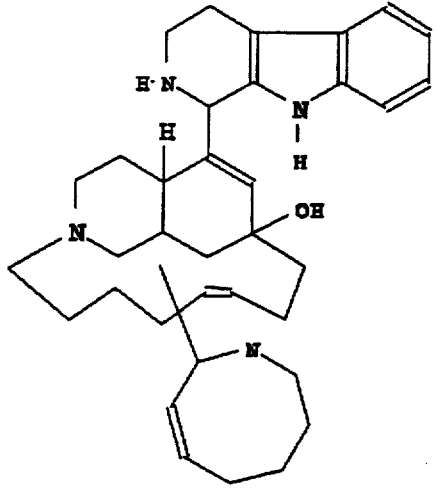 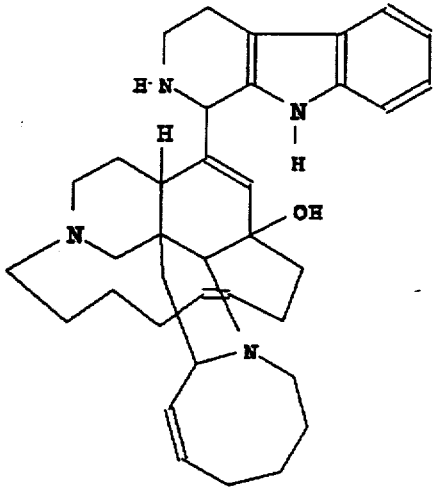

UNITED STATES PATENT AND TRADEMARK OFFICE
CERTIFICATE OF CORRECTION

PATENT NO.  :   4,895,853

DATED       :   January 23, 1990

INVENTOR(S) :   Tatsuo Higa, Ryuichi Sakai, Shigeo Kohmoto, May S. Lui

It is certified that error appears in the above-identified patent and that said Letters Patent is hereby corrected as shown below:

Column 16:  Claim 5:                                should read

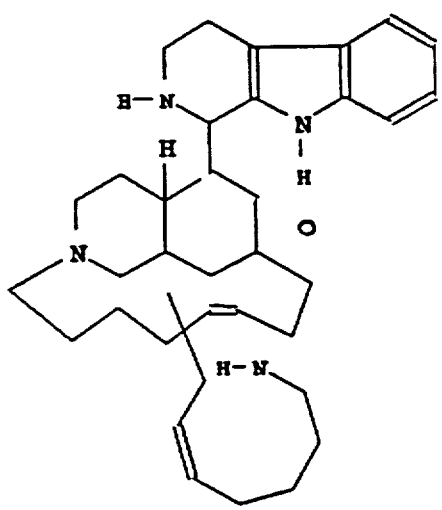
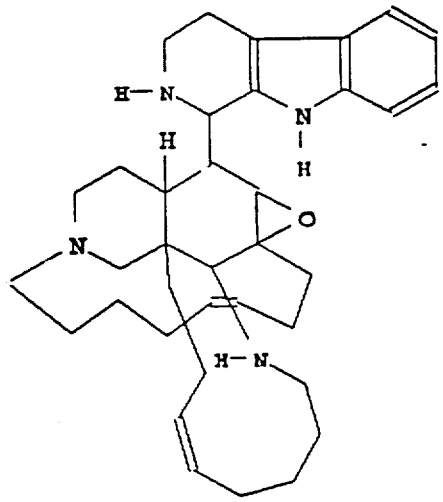

Signed and Sealed this

Twenty-third Day of June, 1992

*Attest:*

DOUGLAS B. COMER

*Attesting Officer*       *Acting Commissioner of Patents and Trademarks*